United States Patent
Hamada

(10) Patent No.: US 8,846,398 B2
(45) Date of Patent: Sep. 30, 2014

(54) METHOD FOR PREPARING HUMAN NEOPLASTICALLY TRANSFORMED CELLS

(71) Applicant: TRDIGM & Co., Ltd., Naha (JP)

(72) Inventor: Katsutomo Hamada, Naha (JP)

(73) Assignee: TRDIGM & Co., Ltd., Naha-shi (JP)

( * ) Notice: Subject to any disclaimer, the term of this patent is extended or adjusted under 35 U.S.C. 154(b) by 0 days.

(21) Appl. No.: 13/690,851

(22) Filed: Nov. 30, 2012

(65) Prior Publication Data

US 2013/0157304 A1    Jun. 20, 2013

(30) Foreign Application Priority Data

May 18, 2010   (JP) ................. 2010-114535

(51) Int. Cl.

| | |
|---|---|
| *C12N 5/10* | (2006.01) |
| *C12N 5/09* | (2010.01) |
| *C12N 5/00* | (2006.01) |
| *C12N 15/85* | (2006.01) |
| *C12Q 1/02* | (2006.01) |
| *G01N 33/50* | (2006.01) |
| *C07K 14/82* | (2006.01) |
| *C12N 9/12* | (2006.01) |

(52) U.S. Cl.
CPC ............ *C12N 15/85* (2013.01); *C12N 2510/04* (2013.01); *C12Q 1/025* (2013.01); *G01N 33/5011* (2013.01); *C07K 14/82* (2013.01); *C12N 9/1276* (2013.01); *C12N 2710/22022* (2013.01)
USPC ............................ 435/377; 435/363; 435/455

(58) Field of Classification Search
CPC .................................................. C12N 2510/04
USPC ......................................... 435/377, 363, 455
See application file for complete search history.

(56) References Cited

U.S. PATENT DOCUMENTS

2003/0087818 A1*   5/2003   Jiang et al. ................... 514/12

FOREIGN PATENT DOCUMENTS

| JP | 2008-109889 A | 5/2008 |
| JP | 2011239726 | * 12/2011 |

OTHER PUBLICATIONS

Leffers et al Nucleic Acids Res. Mar. 25, 1993;21(6):1449-55.The sequence of 28S ribosomal RNA varies within and between human cell lines.*
Hahn et al., Mol Cell Biol. Apr. 2002;22(7):2111-23.Enumeration of the simian virus 40 early region elements necessary for human cell transformation.*
Sáenz-Robles et al., Review Transforming functions of Simian Virus 40 Oncogene (2001) 20, 7899_7907.*
Jat et al., Recombinant Retroviruses Encoding Simian Virus 40 Large T Antigen and Polyomavirus Large and Middle T AntigensMolecular and Cellular Biology, Apr. 1986, p. 1204-1217.*
Sun et al Neoplasia. Jun. 2005;7(6):585-93. The minimal set of genetic alterations required for conversion of primary human fibroblasts to cancer cells in the subrenal capsule assay.*
William C. Hahn et al., "Creation of Human Tumour Cells with Defined Genetic Elements", Letter, Nature, vol. 400, Jul. 29, 1999, pp. 464-468.
Katsutomo Hamada, "Morphological Transformation Caused by a Partial Sequence of U5 Small Nuclear RNA", Molecular Carcinogenesis,1997, pp. 175-188.
Katsutomo Hamada et al., "Effect of Transforming RNA on the Synthesis of a Protein with a Secretory Signal Sequence in Vitro", The Journal of Biological Chemistry, vol. 274, No. 22, May 28, 1999, pp. 15786-15796.
Office Action issued in corresponding Japanese patent application No. 2010-114535 dated Apr. 1, 2014.
Sun et al.—"The Minimal Set of Genetic Alterations Required for Conversion of Primary Human Fibroblasts to Cancer Cells in the Subrenal Capsule Assay", Neoplasia, vol. 7, No. 6, Jun. 2005, pp. 585-593.

* cited by examiner

*Primary Examiner* — Maria Leavitt
(74) *Attorney, Agent, or Firm* — Oblon, Spivak, McClelland, Maier & Neustadt, L.L.P.

(57) ABSTRACT

A method for preparing neoplastically transformed cells from human-derived cells, including the step of introducing human telomerase catalytic subunit (hTERT) gene, SV40 small T antigen (SV40ST) gene, and an antisense oligonucleotide derived from human 28S rRNA into the human-derived cells. The method for preparing neoplastically transformed cells from human-derived cells can be utilized when a variety of human normal cells are induced to be neoplastically transformed in order to elucidate cancer onset mechanisms, so that the method can be effectively utilized in search of target molecules for a new medicament.

5 Claims, 7 Drawing Sheets

METHOD FOR PREPARING HUMAN NEOPLASTICALLY TRANSFORMED CELLS

BACKGROUND OF THE INVENTION

1. Field of the Invention

The present invention relates to a method for preparing human neoplastically transformed cells. More specifically, the present invention relates to a method for preparing neoplastically transformed cells from human-derived cells using antisense RNA derived from human 28S rRNA, cells obtained by the method, a kit for use in the method, and a method of using the cells obtained by the method in assessment of pharmacologically efficacy of an anticancer agent.

2. Discussion of the Related Art

From the studies of human-derived cells using an oncogene encoding a DNA tumor virus protein, such as a Simian virus 40 (SV40) large T antigen, an adenovirus E1A or E1B, Human papillomavirus E6 or E7, a model of carcinogenesis presumes that malignant transformation of human cultured cells consists of two phases of an immortalization process and a tumorigenetic process.

In the immortalization process, telomeric sequences are added to end parts of chromosomes by telomerase activity, thereby making it possible to acquire an infinite lifespan. Therefore, if immortalization takes place, a clonal expansion of cells takes place, so that opportunity for additional genetic alterations is increased, thereby increasing a possibility of tumorigenetic conversion. In addition, in the tumorigenetic process, the immortally transformed cells acquire an autonomous growth potential in the absence of certain growth factors.

Generally, cancer cells express uncertain phenotypes different from normal cells, e.g. genomic instability, lack of responsiveness to the chemical signalings, and loss of differentiation. However, it yet remains obscure whether those alterations involved in the tumorigenetic process described above result from cumulative mutations in genes related to the particular proteins, or a cascade of gene expression initiated by a factor activated in the onset of tumorigenesis about which little is known.

In recent years, it has been reported that normal human cells can be transformed by expression of human telomerase catalytic subunit (hTERT), SV40 early region (ER), and activated H-ras gene (See W. C. Hahn et al, "Creation of human tumour cells with defined genetic elements." letter, Nature, 29 Jul. 1999). According to the report, in the presence of hTERT, the SV40 large T antigen (LT) inactivates retinoblastoma protein (pRB) tumor suppressor pathway and p53 tumor suppressor pathway, and the SV40 small T antigen (ST) serves to dysfunction phosphatase 2A. Also, the activated ras gene is known to participate in the tumorigenecity of transformed cells. Therefore, the aberrations are suggested to be the minimal number of genetic events required in the malignant conversion of human-derived cells.

In addition, Japanese Patent Laid-Open No. 2008-109889 discloses a method for inducing neoplastic transformation of human-derived cells, including expressing Src in the presence of hTERT and an SV40 large T antigen (LT).

On the other hand, the present inventors have previously reported that a nucleotide sequence resulting from addition of a poly(A) chain to a certain nucleotide sequence at a 3'-end side of a first stem of a secondary structure of U5 small nuclear RNA [also named as transforming RNA (TR)] is expressed as non-coding mRNA, thereby making it possible to drive rat fibroblastic 3Y1 cells into the neoplastically transformed cells, i.e. tumor cells (See K. Hamada, "Morphological transformation caused by a partial sequence of U5 small nuclear RNA." Mol. Carcinog., 1997, 20, 175-188). The 3Y1 cells had already acquired the ability to proliferate infinitely through spontaneous immortalization. Therefore, it is deduced that the TR plays a role in tumorigenesis, not in immortalization; as a result of further studies in view of the above, the present inventors have found that the above-mentioned transformation is greatly dependent on a certain polypurine sequence ggagaggaa (SEQ ID NO: 3) of the TR.

Furthermore, it is reported that as a result of studies using a rabbit reticulocyte extract, the TR sequence synthesized in vitro directly binds to 28S rRNA of ribosome in the nascent chain elongation of peptide synthesis to affect secretory signal peptide-associated translation (K. Hamada et al, "Effect of Transforming RNA on the Synthesis of a Protein with a Secretory Signal Sequence in Vitro." J. Biol. Chem., 1999, 274(22), 15786-15796). Moreover, it is found that the oligodeoxynucleotides (ODNs) containing the above-mentioned polypurine sequence bind to cucc sequence (SEQ ID NO: 4) on 28S rRNA, and on the other hand that the oligodeoxynucleotides (ODNs) containing an antisense sequence of the above polypurine sequence bind to gagg (nucleotides 48 to 51) (SEQ ID NO: 5) on 7SL RNA of signal recognition particle (SRP). In view of the above, it is considered that the chain elongation arrest activity influences physiological actions between the 28S rRNA and the SRP RNA.

However, it has been found that the above-mentioned TR cannot be induced into neoplastically transformed cells by transforming human-derived cells in the presence of hTERT, depending upon a combination with c-myc, an activated H-ras, or a gene encoding SV40 Large T or the like.

An object of the present invention is to provide a method for preparing neoplastically transformed cells from human-derived cells, cells obtained by the method, a kit for use in the method, and a method of using cells obtained by the method in assessment of pharmacological efficacy of an anticancer agent, which are free from any safety problems.

These and other objects of the present invention will be apparent from the following description.

SUMMARY OF THE INVENTION

As a result of intensive studies in order to solve the above problems, the present inventors have found that a certain antisense short chain RNA complementary to human 28S rRNA binds on a ribosome surface as a human-specific transforming RNA (hTR), so that human-derived cells can be transformed and induced into neoplastically transformed cells, and the present invention is perfected thereby.

In sum, the present invention relates to:

[1] a method for preparing neoplastically transformed cells from human-derived cells, including the step of introducing human telomerase catalytic subunit (hTERT) gene, SV40 small T antigen (SV40ST) gene, and an antisense oligonucleotide derived from human 28S rRNA into human-derived cells;

[2] a method for introducing a gene for neoplastically transforming human-derived cells, including incorporating human telomerase catalytic subunit (hTERT) gene, SV40 small T antigen (SV40ST) gene, and an antisense oligonucleotide derived from human 28S rRNA into the same or different vectors, and introducing the genes into human-derived cells therewith;

[3] neoplastically transformed cells derived from human-derived cells, obtained by the method as defined in the above [1];

[4] a kit for use in the method as defined in the above [1], containing human telomerase catalytic subunit (hTERT) gene, SV40 small T antigen (SV40ST) gene, and an antisense oligonucleotide derived from human 28S rRNA;

[5] a method for screening an anticancer agent, including the steps of culturing neoplastically transformed cells from human-derived cells obtained by the method as defined in the above [1] in the presence or absence of a candidate compound, and judging that the candidate compound has a high possibility of having an action as an anticancer agent in a case where the neoplastically transformed cells that are cultured in the presence of the candidate compound have a larger degree of inhibition of neoplastic transformation from human-derived cells, as compared to the neoplastically transformed cells that are cultured in the absence thereof; and

[6] a method for screening an anticancer agent, including the steps of culturing human-derived cells into which the genes are introduced according to the method as defined in the above [2] in the presence or absence of a candidate compound, and judging that the candidate compound has a high possibility of having an action as an anticancer agent in a case where the neoplastically transformed cells that are cultured in the presence of the candidate compound have a larger degree of inhibition of neoplastic transformation from human-derived cells, as compared to the neoplastically transformed cells that are cultured in the absence thereof.

According to the method for preparing neoplastically transformed cells from human-derived cells of the present invention, human-derived cells can be more safely induced into neoplastically transformed cells having a potent neoplastically transforming ability.

BRIEF DESCRIPTION OF THE DRAWINGS

FIG. 1-$a$ shows a putative secondary structure of domain 5 of human 28S rRNA, wherein the left side is a V8-4 region, and the right side is the entire domain 5, and wherein the lower rows show nucleotide sequences of asR70 (SEQ ID NO: 1), asR56 (SEQ ID NO: 6), asR46 (SEQ ID NO: 2), and sR70 (SEQ ID NO: 7). FIG. 1-$b$ is a view showing the assessment results of cleavage with RNase H when co-cultured with the oligonucleotide (ON), wherein a left side shows the results of rabbit lysates, and a right side shows the results of human cell extracts. FIG. 1-$c$ shows binding properties of asR70, asR56, and sR70, wherein as to asR70, starting from left, the results of the asR70 probe alone, untreated RNA ($2.0 \times 10^5$ cpm of the asR70 probe being added), ODN-treated RNA ($2.0 \times 10^5$ cpm of the asR70 probe being added), untreated RNA ($1.0 \times 10^5$ cpm of the asR70 probe being added), ODN-treated RNA ($1.0 \times 10^5$ cpm of the asR70 probe being added) are shown; as to asR56, starting from left, the results of the asR56 probe alone, ODN-treated RNA ($2.0 \times 10^5$ cpm of the asR56 probe being added), ODN-treated RNA ($1.0 \times 10^5$ cpm of the asR56 probe being added), untreated RNA ($2.0 \times 10^5$ cpm of the asR56 probe being added) are shown; and as to sR70, starting from left, the results of the sR70 probe alone, ODN-treated RNA ($2.0 \times 10^5$ cpm of the sR70 probe being added), ODN-treated RNA ($1.0 \times 10^5$ cpm of the sR70 probe being added), and untreated RNA ($2.0 \times 10^5$ cpm of the sR70 probe being added) are shown. Here, the results of one in which total RNA is treated with 20 units of RNaseH.

FIG. 2-$b$ is views showing, starting from an upper row, the results of hTERT (TRAP assay), the results for asR70 (RT-PCR), and the results of SV40ST (immunoblotting). FIG. 2-$c$ is graphs showing influences on the growth of the transformed cells of the oligonucleotides derived from ribosome. The graphs show the cell condition after 4.5 months from the introduction, wherein the left graph shows cell growth, and the right graph shows cell density. FIG. 2-$d$ shows the results of colony formation test of the transformed cells. The photographs show general examples of each of large colonies, middle colonies, and small colonies, starting from left.

FIG. 4-$a$ is views showing the results of assessing synthesizing rates of Bip, fibronectin, and integrin β1, according to pulse-chase labeling and immunoprecipitation using $^{35}$S-methionine. FIGS. 4-$b$ and 4-$c$ are views showing the results of immunoblotting of Bip, eIF2α, phosphorylated eIF2α, and ATF4.

DETAILED DESCRIPTION OF THE INVENTION

The method for preparing neoplastically transformed cells from human-derived cells includes the step of introducing human telomerase catalytic subunit (hTERT) gene, and SV40 small T antigen (SV40ST) gene into human-derived cells, and the method has a great feature in that the antisense oligonucleotide derived from human 28S rRNA is used together during the step.

Figure 1A:
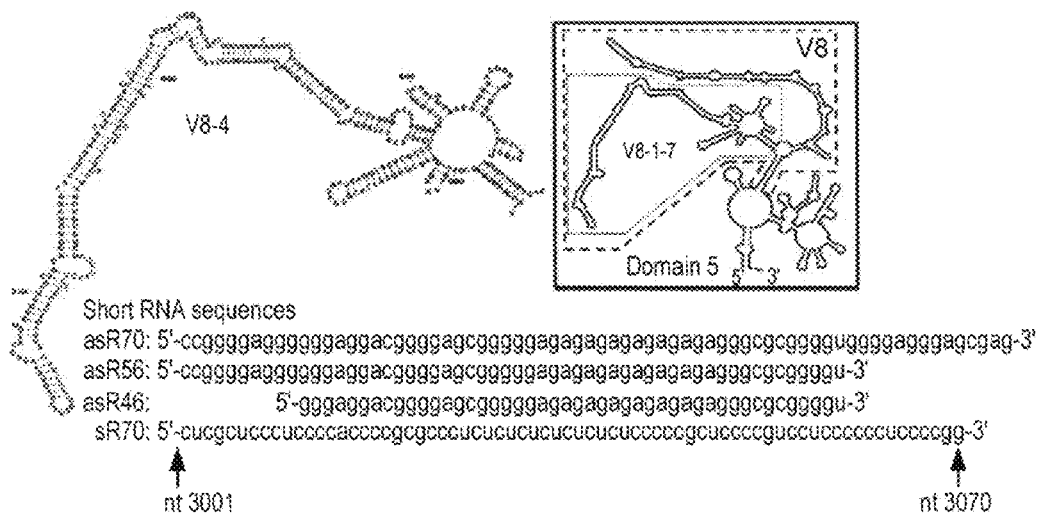
FIG. 1 is views showing the results of interaction between human 28S rRNA and antisense short RNAs.
Figure 1B:
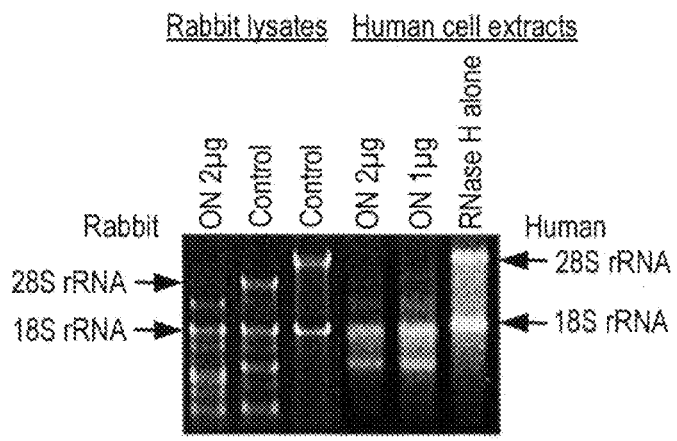
Figure 1C:
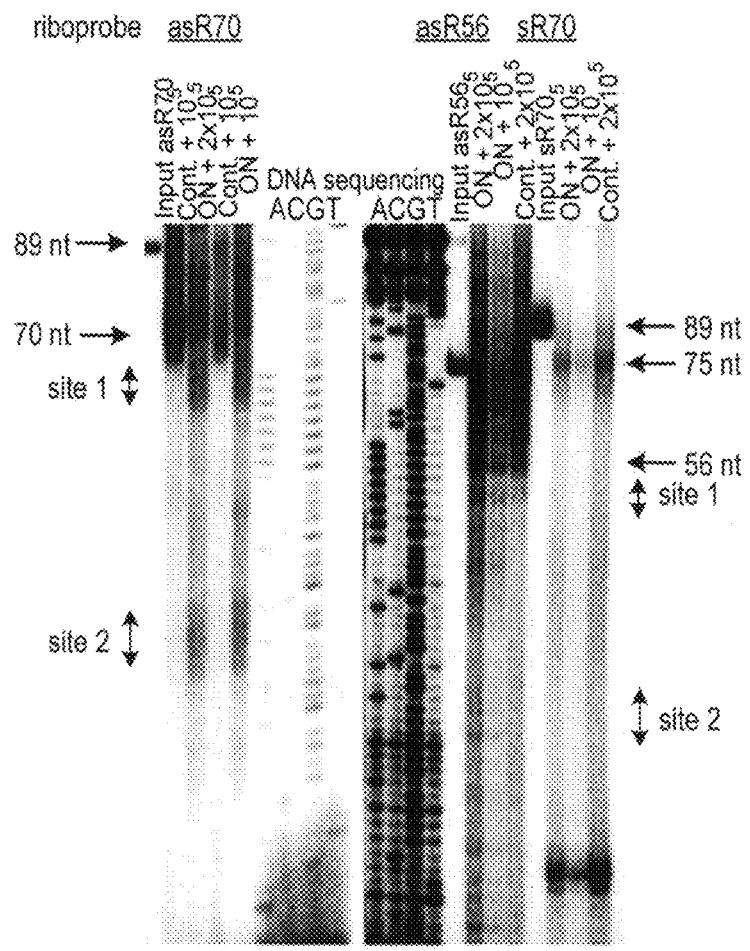
Figure 2A:
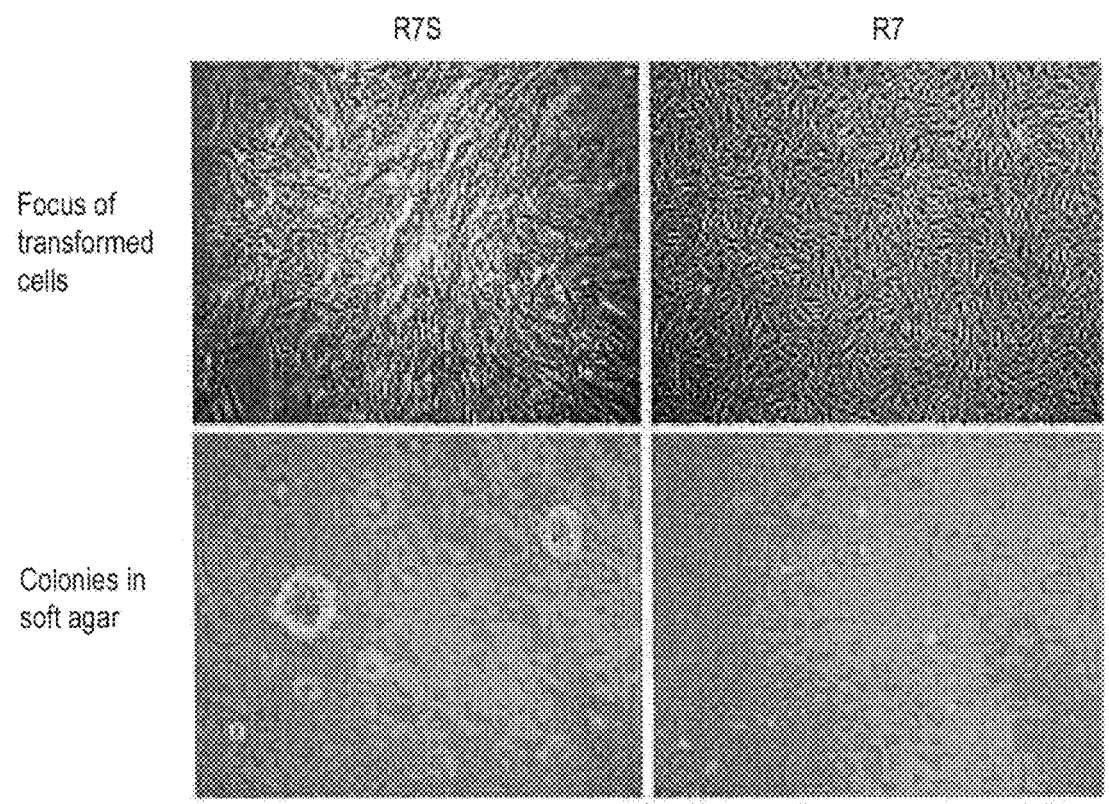
FIG. 2-$a$ is views showing the morphologies of the transformed cells and colony formation in a soft agar medium, wherein the left side shows cells transformed with hTERT, SV40ST, and asR70 (R7S), and the right side shows cells transformed with hTERT and asR70 (R7), and wherein an upper row is views showing cell morphologies, and a lower row is views showing colony formation.
Figure 2B:
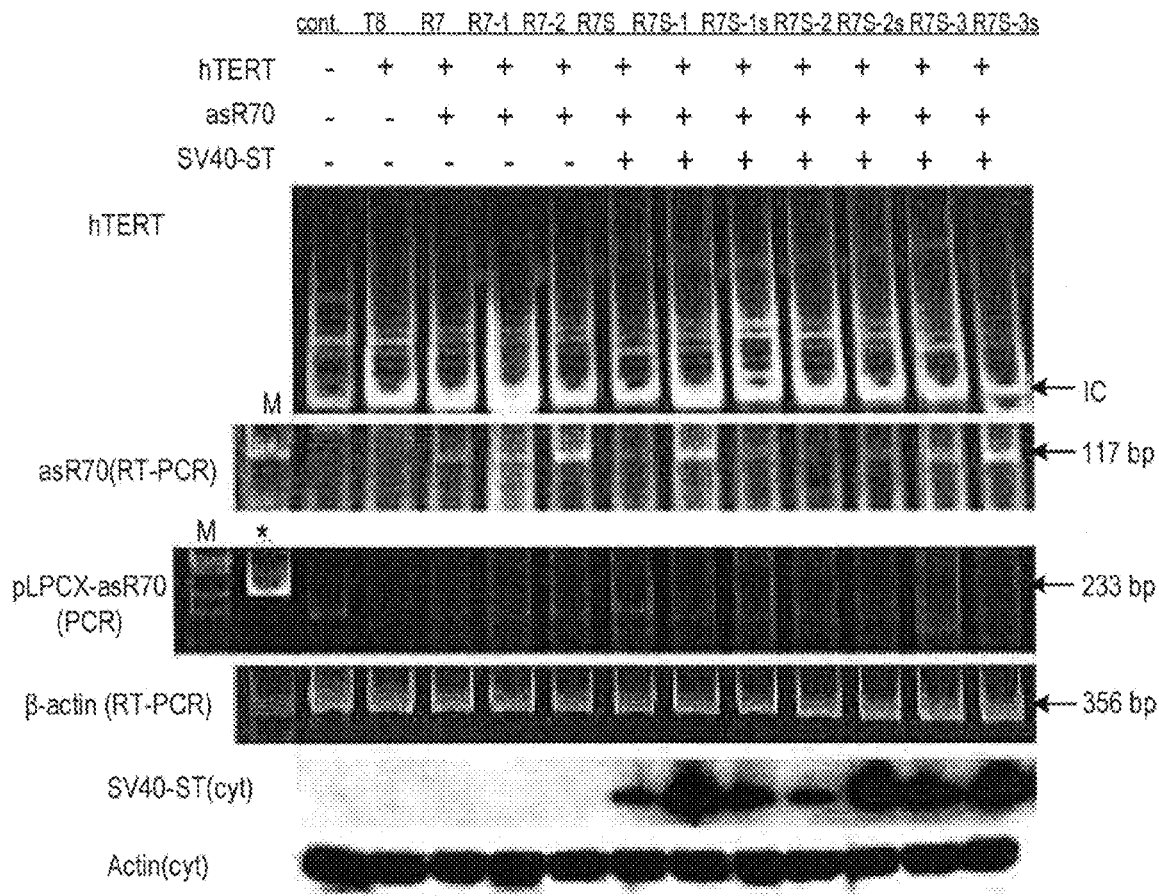
Figure 2C:
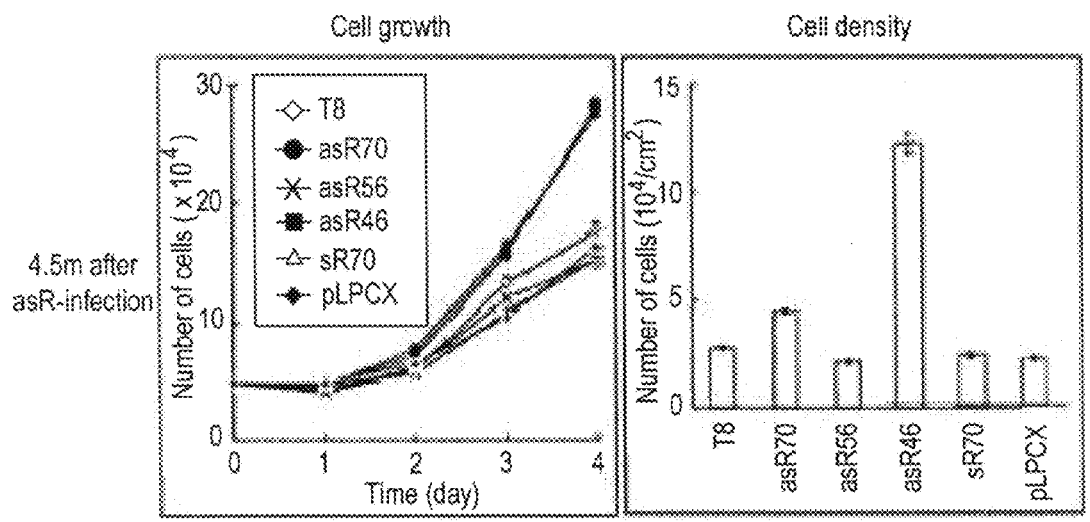
Figure 2D:
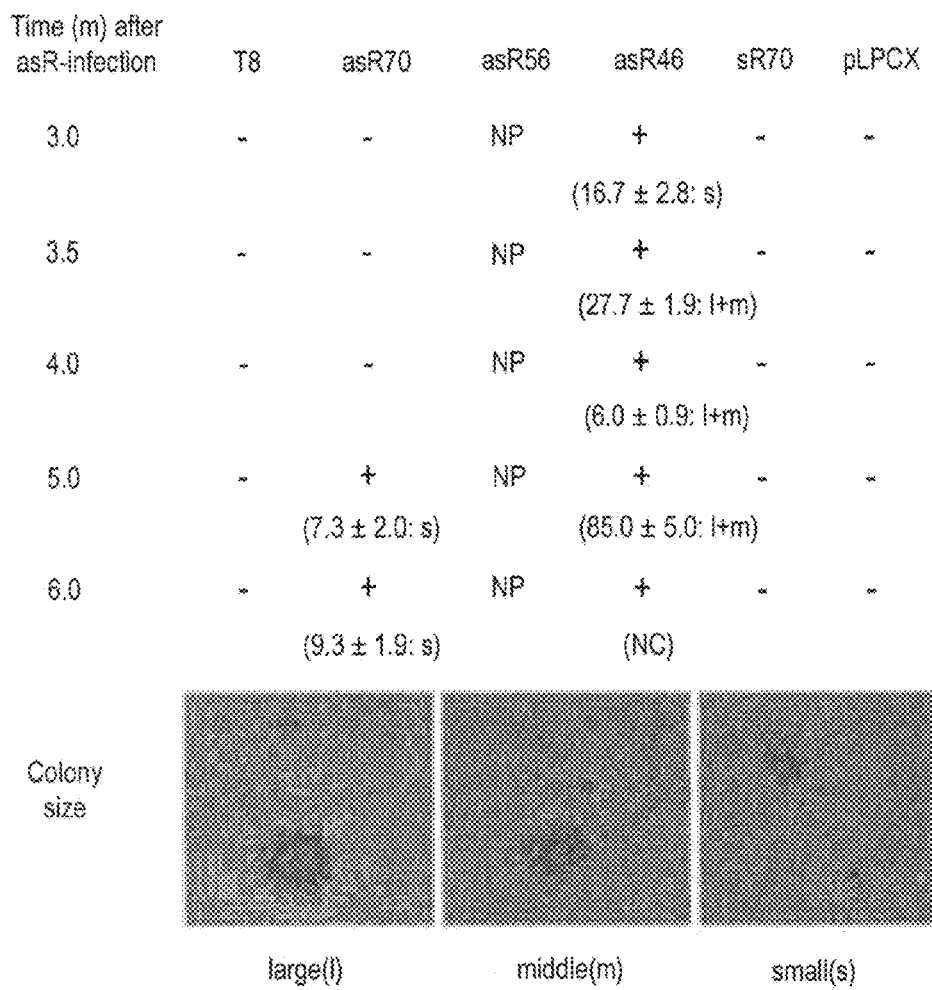

The V8-4 region of the domain 5 is located at an about 3 kb-region from the 5' end of human 28S rRNA (see FIG. 1-$a$). The V8 region corresponds to yeast ES27 that has been reported to have an action of moving nonribosomal factors such as chaperones, modifying enzymes, SRP or translocon (protein transport device on the endoplasmic reticulum membrane) from the L1 side on the ribosome toward the tunnel exit site. In addition, the V8-4 region contains six cucc sequences (SEQ ID NO: 4) in the latter half of the 5' end side. Therefore, as a result of comprehensively judging these phenomena, the present inventors have considered that short RNA complementary to ES27 of human 28S rRNA can be used as human transforming RNA (hTR), and that when the hTR is used together with hTERT and SV40ST, they have surprisingly found out that human-derived cells can be transformed. The resulting transformed cells acquired anchorage-independent growth potential and showed chromosomal aberrations, thereby making it possible to introduce hTERT and SV40ST with the hTR, which suggests that the human-derived cells can be transformed into neoplastically transformed cells.

The method for preparing neoplastically transformed cells from human-derived cells of the present invention includes the step of introducing human telomerase catalytic subunit (hTERT) gene, SV40 small T antigen (SV40ST) gene, and an antisense oligonucleotide derived from human 28S rRNA into human-derived cells.

The term "gene" as used herein refers to a factor that plays a role of gene information of an organism, which is meant to be used to include DNA and RNA. In addition, the term "nucleotide" is meant to be used to include DNA and RNA. Also, the term "antisense oligonucleotide" refers to an oligonucleotide having a nucleotide sequence complementary to a certain nucleotide sequence (hereinafter referred to as sense sequence), and capable of hybridizing to the sense sequence.

The human telomerase catalytic subunit (hTERT) gene is not particularly limited, and includes those known in the field of art. The telomerase is an enzyme that maintains a telomeric length by being antagonistic to the shortening of the telomeric length by cell division. The telomerase contains as constituents RNA serving as a template of the telomeric sequence, and a reverse transcriptase, and this reverse transcriptase moiety is hTERT.

The SV40 small T antigen (SV40ST) gene is not particularly limited, and includes those known in the field of art. The SV40 (Simian virus 40) is a virus belonging to Polyomavirus, and is separated from Rhesus monkey kidney cells, and this virus produces a large T antigen and a small T antigen as early stage proteins at an early infection stage to cells (before DNA synthesis takes place). In the present invention, the small T antigen is used as an antigenic virus.

The antisense oligonucleotide derived from human 28S rRNA includes an antisense oligonucleotide of a sense sequence in the expansion segment 27 (ES27) region of human 28S rRNA. Among them, an oligonucleotide containing the nucleotide sequence shown in SEQ ID NO: 1, an oligonucleotide containing the nucleotide sequence shown in SEQ ID NO: 2, and an oligonucleotide containing the nucleotide sequence shown in SEQ ID NO: 6 are preferred; an oligonucleotide essentially consisting of the nucleotide sequence shown in SEQ ID NO: 1, an oligonucleotide essentially consisting of the nucleotide sequence shown in SEQ ID NO: 2, and an oligonucleotide essentially consisting of the nucleotide sequence shown in SEQ ID NO: 6 are more preferred; and an oligonucleotide consisting of the nucleotide sequence shown in SEQ ID NO: 1 and an oligonucleotide consisting of the nucleotide sequence shown in SEQ ID NO: 2 are even more preferred.

In addition, in the present invention, as the above-mentioned oligonucleotide, an oligonucleotide having deletion, addition, insertion or substitution of one or more nucleotides in the above-mentioned nucleotide sequence is also preferably used. Concretely, the oligonucleotide includes an oligonucleotide having homology of at least 70% or more, preferably 80% or more, more preferably 90% or more, and even more preferably 95% or more, to the oligonucleotide shown in the above-mentioned nucleotide sequence, or an oligonucleotide containing the oligonucleotide. Also, the nucleotide length is not particularly limited, and the nucleotide length is preferably from 40 to 200, more preferably from 40 to 150, even more preferably from 40 to 100, even more preferably from 40 to 90, even more preferably from 40 to 80, and even more preferably from 46 to 70. The oligonucleotide as described above exhibits similar effects (capable of neoplastically transforming human-derived cells at an equivalent level) to the cases of using the oligonucleotide consisting of the nucleotide sequence shown in SEQ ID NO: 1, the oligonucleotide consisting of the nucleotide sequence shown in SEQ ID NO: 2, and the oligonucleotide consisting of the nucleotide sequence shown in SEQ ID NO: 6. Here, the term homology as used herein can be obtained by, for example, using a search program BLAST in which an algorithm developed by Altschul et al. (*The Journal of Molecular Biology*, 215, 403-410 (1990)) is employed.

A schematic view of an oligonucleotide consisting of the nucleotide sequence shown in SEQ ID NO: 1, an oligonucleotide consisting of the nucleotide sequence shown in SEQ ID NO: 2, and an oligonucleotide consisting of the nucleotide sequence shown in SEQ ID NO: 6 is shown in FIG. 1. These oligonucleotides are an antisense oligonucleotide to an oligonucleotide shown by 3001 to 3070 nucleotides (hereinafter also referred to as asR70), an antisense oligonucleotide to an oligonucleotide shown by 3015 to 3060 nucleotides (hereinafter also referred to as asR46), and an antisense oligonucleotide to an oligonucleotide shown by 3015 to 3070 nucleotides (hereinafter also referred to as asR56), each located in the domain 5 of human 28S rRNA. All the oligonucleotides are complementary to a sense sequence located in the expansion segment 27 (ES27, 2889 to 3551 nucleotides) region, which are suggested to partake in the function of ES27, in other words, proliferation. Here, the abbreviation asR as used herein means antisense short RNA, and the abbreviation sR means sense short RNA.

The method for synthesizing an antisense oligonucleotide derived from human 28S rRNA is not particularly limited, and a phosphoramidite method, a phosphorothioate method, a phosphotriester method or the like, using a known oligonucleotide synthesizer can be employed.

The gene and the antisense oligonucleotide mentioned above may be a modified or substituted product in accordance with a known method within the range so as not to markedly lower its activity, in order to increase stability and affinity to the cells. For example, the gene and the antisense oligonucleotide can be also used in the form of a derivative formed by substituting a phosphate group, or a hydroxyl group or hydroxyl groups of a ribose moiety, with another stable group.

The human-derived cells into which the gene and the antisense oligonucleotide described above are introduced are not particularly limited, and include human fibroblast cells, human endothelial cells, human epithelial cells, and the like. The derivations or tissues of the above-mentioned cells are not particularly limited.

The method of introducing the gene and the antisense oligonucleotide mentioned above into human-derived cells is not particularly limited. For example, a product obtained by incorporating the gene and the antisense oligonucleotide mentioned above into any vector can be used.

It is preferable that the vector is self-replicable in a host cell, and at the same time contains, in addition to the gene and the antisense oligonucleotide mentioned above, a promoter and a transcription termination sequence. In addition, the vector may contain a gene controlling a promoter. Here, the promoter is not particularly limited so long as the gene and the antisense oligonucleotide mentioned above can be expressed in a host cell.

The preferred vector usable in the present invention includes, for example, adenoviral vector, Vaccinia virus vector, retrovirus vector and the like.

The gene and the antisense oligonucleotide mentioned above may be introduced at the same time, collectively or individually, and they may each be introduced at a different timing. The gene and the antisense oligonucleotide mentioned above may be introduced into separate vectors and used, or may be introduced into the identical vector and used. In a case where the gene and the antisense oligonucleotide incorporated into separate vectors are used, for example, those in which hTERT gene is incorporated into pBABE vector, those in which SV40ST gene is incorporated into pLHCX vector, and those in which an antisense oligonucleotide is incorporated into pLPCX vector can be used. Also, in a case where the gene and the antisense oligonucleotide incorporated into the identical vector are used, a preferred vector includes retroviral vector, and the locations of the gene and the antisense oligonucleotide mentioned above in the vector are not particularly limited, and for example, the gene and the antisense oligonucleotide are located between a promoter and a transcription termination sequence, in the order of hTERT gene, SV40ST gene, and the antisense oligonucleotide, starting from the promoter side.

The method for introducing a vector includes an electroporation method, a calcium phosphate method, a lipofection method and the like.

In addition, the vector may be introduced by preparing a vector obtained by further incorporating viral DNA for infection to the introduced cells into the above-mentioned vector, thereby infecting human-derived cells with the vector-introduced virus. The virus for infection includes adenovirus, adeno-associated virus, retrovirus, and the like.

Here, the method of constructing the vector, a concrete method of using the vector, and the like may be referred to, for example, textbooks such as Sambrook, J., et. al., *Molecular Cloning: A Laboratory Manual*; $2^{nd}$ Ed., Cold Spring Harbor Laboratory, Cold Spring Harbor. N.Y., 1989.

Thus, hTERT gene, SV40ST gene, and an antisense oligonucleotide derived from human 28S rRNA can be introduced into human-derived cells. The cells obtained are formed into transformed cells which express a protein encoded by hTERT and SV40ST, and at the same time express the antisense oligonucleotide derived from human 28S rRNA. Therefore, the present invention provides cells obtained by introduction of the hTERT gene, the SV40ST gene, and the antisense oligonucleotide derived from human 28S rRNA. The cells may be cultured under conditions appropriate for the cells to repeat population doubling, and screened with a known agent. Here, in the present invention, those obtained by introducing SV40ST gene and an antisense oligonucleotide derived from human 28S rRNA into hTERT immortalized cells into which hTERT gene is already incorporated are also embraced within the scope of the present invention. The condition of human-derived cells in which neoplastic transformation is induced by hTERT gene, SV40ST gene, and an antisense oligonucleotide derived from human 28S rRNA can be confirmed in accordance with a method described in Examples set forth below.

In addition, in the present invention, human-derived cells can be neoplastically transformed by using hTERT gene, SV40ST gene, and an antisense oligonucleotide derived from human 28S rRNA in combination, so that a kit containing hTERT gene, SV40ST gene, and an antisense oligonucleotide derived from human 28S rRNA can be used in the neoplastic transformation of human-derived cells. The present invention also provides a kit containing hTERT gene, SV40ST gene, and an antisense oligonucleotide derived from human 28S rRNA.

Furthermore, the neoplastic transformation of human-derived cells is facilitated by using hTERT gene, SV40ST gene, and an antisense oligonucleotide derived from human 28S rRNA in combination, and since a degree of neoplastic transformation is at a certain level, human-derived cells that are neoplastically transformed using hTERT gene, SV40ST gene, and an antisense oligonucleotide derived from human 28S rRNA, or human-derived cells into which hTERT gene, SV40ST gene, and an antisense oligonucleotide derived from human 28S rRNA are introduced, can be used in screening an anticancer agent. Therefore, the present invention provides a method of screening an anticancer agent. The above-mentioned method is an in vitro assessment in the human system, assumption to in vivo assessment is facilitated, so that an effective substance can be found more conveniently and quickly.

A concrete method includes a method including the steps of:

contacting a candidate compound with the neoplastically transformed cells obtained by introducing hTERT gene, SV40ST gene, and an antisense oligonucleotide derived from human 28S rRNA into human cells, and judging that the candidate compound has a high possibility of having an action as an anticancer agent in a case where the cells after contacting the candidate compound has a smaller degree of neoplastic transformation than the cells before contacting the candidate compound.

More specifically, there are two embodiments:

an embodiment of culturing neoplastically transformed cells from human-derived cells obtained by introducing hTERT gene, SV40ST gene, and an antisense oligonucleotide derived from human 28S rRNA into human-derived cells in the presence or absence of a candidate compound, and judging that the candidate compound has a high possibility of having an action as an anticancer agent in a case where the neoplastically transformed cells that are cultured in the presence of the candidate compound have a larger degree of inhibition of neoplastic transformation from human-derived cells, as compared to the neoplastically transformed cells that are cultured in the absence thereof (Embodiment 1); and an embodiment of comprising culturing human-derived cells into which the above genes are introduced in the presence or absence of a candidate compound, and judging that the candidate compound has a high possibility of having an action as an anticancer agent in a case where the neoplastically transformed cells that are cultured in the presence of the candidate compound have a larger degree of inhibition of neoplastic transformation from human-derived cells, as compared to the neoplastically transformed cells that are cultured in the absence thereof (Embodiment 2).

In Embodiment 1 and Embodiment 2, the conditions for culturing the cells in the presence or absence of the candidate compound can be carried out in the same manner according to known conditions when culturing the cells before the above genes are introduced, except for the presence or absence of the candidate compound, and are not particularly limited.

In Embodiment 1, when it is judged that the candidate compound has a high possibility of having an action as an anticancer agent, in a case where a part of the cells cultured in the presence of the candidate compound is found to undergo changes such as transformed morphological losses, induction of apoptosis, and anchorage-independent losses, as compared to the cells cultured in the absence thereof, a candidate compound to which the cells are contacted has an action as an anticancer agent, so that the candidate compound can be judged to have an effect of reducing neoplastic transformation.

In Embodiment 2, when it is judged that the candidate compound has a high possibility of having an action as an anticancer agent, in a case where a part of the cells cultured in the presence of the candidate compound is found to have a smaller degree of population doubling and change in cell morphologies, as compared to the cells cultured in the absence thereof, a candidate compound to which the cells are contacted has an action as an anticancer agent, so that the candidate compound can be judged to have an effect of reducing neoplastic transformation.

EXAMPLES

The present invention will be explained hereinbelow on the basis of Examples, without intending to limit the present invention to these Examples and the like. Here, hTERT gene was obtained from Dr. F. Ishikawa or Addgene 1774, SV40ST gene was obtained from JCRB gene bank (pMTI0D), and the oligonucleotide derived from human 28S rRNA was synthesized herein or obtained from Takara Bio Inc., and each was used. In addition, human fibroblast cells (MJ90 cells) were obtained from Dr. O. M. Pereira-Smith, and human fibroblast cells (TIG3 cells) were obtained from RB cell bank, and used.

Reference Example 1

Binding Properties of ggagaggaa Sequence (SEQ ID NO: 3)

To 10 μL of a rabbit lysate or 20 μL of a human-derived cell extract was added a polypurine sequence ggagaggaa (SEQ ID NO: 3), a partial nucleotide sequence of transforming RNA (TR), and allowed to react in the presence of RNase H. Thereafter, total RNA was collected and electrophoresed on polyacrylamide gel. The results are shown in FIG. 1-b. As a result, it can be seen that the ggagaggaa sequence (SEQ ID NO: 3) is bound to 28S rRNA.

Reference Example 2

Binding Properties of asR70, asR56, and sR70

The binding properties of asR70, asR56, and sR70 were assessed in accordance with the following method. The results are shown in FIG. 1-c. Concretely, first, plasmids pG-asR70, pG-asR56, and pG-sR70 were prepared by insertions thereof into a plasmid pGEM3 (manufactured by Promega) cleaved with HindIII-XbaI, and labeled RNA probes (riboprobes) of asR70, asR56, and sR70 were produced from the plasmids obtained using SP6 RNA polymerase (manufactured by Takara Bio Inc.) and [$\alpha$-$^{32}$P]-GTP (manufactured by Perkin-Elmer). The probes obtained were electrophoresed on polyacrylamide gel, and as a result, the asR70 probe had a length of 89 nucleotides (first lane from left), the asR56 probe had a length of 75 nucleotides (eighth lane from right), and the sR70 probe had a length of 89 nucleotides (fourth lane from right).

Next, 20 μL of the human cell lysate and 4 μg of an oligodeoxynucleotide ggagaggaa (SEQ ID NO: 3) were mixed, and cleaved with RNase H, and thereafter the collected total RNA was mixed with riboprobes of asR70, asR56, and sR70, and treated with RNase A and RNase $T_1$. Here, as a comparison, an example in which the oligodeoxynucleotide ggagaggaa (SEQ ID NO: 3) was not used was also treated in the same manner.

The oligodeoxynucleotide-treated total RNA showed two cleavage sites in the binding with the asR70 probe. In other words, it was found that the oligodeoxynucleotide ggagaggaa (SEQ ID NO: 3) has binding sites within 3001 to 3070 nucleotides of 28S rRNA (third to fifth lanes from left). Concretely, it could be seen that the cucc sequence (SEQ ID NO: 4, site 1), corresponding to 3063 to 3066 nucleotides of 28S rRNA and the cucucu sequence (SEQ ID NO: 8, site 2), corresponding to 3035 to 3040 nucleotides thereof could be bound. In addition, asR56 shorter by 14 nucleotides was found to be bound in the same sites (sixth to seventh lanes from right). The sites 1 and 2 are located approximately 23 to 24 nucleotides apart from each other, in which the site 1 is located at a hairpin loop of the V8-4 region, and the site 2 is located at a bulged part, whereby suggesting that asR70 and asR56 are bound to 28S rRNA at the above two sites. On the other hand, the binding of sR70 probe and 28S rRNA could not be confirmed (second and third lanes from right). In addition, it is shown in K. Hamada et al, *J. Biol. Chem.*, 1999, 274(22), 15786-15796 that the gagagag sequence (SEQ ID NO: 9), a modified sequence of the oligodeoxynucleotide as shown in SEQ ID NO: 3, is incapable of inhibiting the secretory protein synthesis, whereby it is suggested therefrom that the protein synthesis in the V8-4 region is more regulated in the site 1 than in the site 2 by the interaction with RNA of SRP. Here, asR56 contains a sequence in asR70 that binds to the site 2, and it is deduced that the binding is weak with aberrant binding.

Example 1

Morphologies and Neoplastic Transformation of Transformed Cells

Cell morphologies were observed with a phase contrast microscope for MJ90 cells transformed with hTERT, asR70, and SV40ST (hTERT+asR70+SV40ST, also simply R7S), and MJ90 cells transformed with hTERT and asR70 (hTERT+asR70, also simply R7). In addition, a colony formation test was also conducted in a soft agar medium. The results are shown in FIG. 2-a.

Here, the transformed cells prepared in the following manner were used. Concretely, pGEM3 (manufactured by Promega) inserted with asR70 was cleaved with HindIII-EcoRI, and a fragment obtained was inserted into pLPCX (manufactured by Clontech) to prepare a vector named pLPCX-asR70. Also, an SV40ST fragment amplified by PCR was inserted into pLHCX (manufactured by Clontech) to prepare a vector named pLHCX-ST. As the plasmids for hTERT expression, pcDNAhTERTn2 (provided by Dr. F. Ishikawa) and pBABE-neo-hTERT (Addgene plasmid 1774) were used. Next, 293T cells (obtained from Riken Cell Bank) were transfected with pLPCX-asR70 and pLHCX-ST, together with a retrovirus packaging plasmid pCL-10A1 (manufactured by Imgenex), the virus was then collected, and thereafter the MJ90 cells were infected with the virus. In a case where pcDNAhTERTn2 was used, the MJ90 cells were transfected with lipofectamine 2000. In a case where pBABE-neo-hTERT was used, the virus was prepared therewith, and TIG3 cells were infected with the virus. The cells obtained were subjected to drug screening to select the cells having a life span longer than the parental cells to be used in the experiment.

It can be seen from FIG. 2-a that cells R7S transformed with hTERT, SV40ST, and asR70 had indistinct boundaries between the cells, and that colonies were formed even in a soft agar medium at days 14 to 18 after transplantation, so that the transformed cells had anchorage-independent growing ability and underwent neoplastic transformation.

Example 2

Expression of hTERT, SV40ST, and asR70 in Transformed Cells

Intact normal human fibroblastic cells (MJ90), hTERT-immortalized cells (T8), cells co-transfected with hTERT and asR70 (R7), and clones thereof (R7-1 and R7-2) were furnished. In addition, cells prepared by introduction of SV40ST into the cells R7 (R7S), clones thereof (R7S-1, R7S-2, and R7S-3), and subclones thereof (R7S-1s, R7S-2s, and R7S-3s) were also furnished. Here, as for all the furnished cells, cell lines selected in the same manner as in Example 1 were used. In addition, all the cell lines were subjected to a colony formation test in the same manner as in Example 1. As a result, the cells of R7S series were confirmed to form many colonies, but no colonies were formed at all in the cells of R7, R7-1, and R7-2, the cells MJ90, and the cells T8.

The telomerase activity (hTERT activity) was assessed by carrying out TRAP (telomeric repeat amplification protocol)

assay using PCR, with a 1 μg extract of each of the cells. The results are shown in FIG. 2-*b* (an uppermost row of the PCR results). The cells other than the cells MJ90 were shown to have telomerase activity. Here, "IC" in the figure is an internal standard material for PCR.

The asR70 was assessed by carrying out RT-PCR using the following asR70-specific primers (second row from top of the PCR results in FIG. 2-*b*). As a result, 117 bp amplified products were found in the cells other than the cells MJ90 and the cells T8.

```
pLPCX-retroF:
                                         (SEQ ID NO: 10)
5'-cgctagcgctaccggactc-3' asR70-R:
                                         (SEQ ID NO: 11)
5'-ataaagcttctcgctccctccccaccc-3'
```

In addition, in order to confirm that the 117 bp amplified products was specific to asR70 cDNA, amplification was carried out by PCR using the above-mentioned pLPCX-retroF primer, and

```
pLPCX-seqR:
  5'-tggggtctttcattccc-3'             (SEQ ID NO: 12)
``` as a primer specific to the non-transcriptional region of the plasmid harboring asR70 DNA; however, 233 bp amplified products could not be confirmed, so that it could be confirmed that the asR70 is not derived from the plasmid but incorporated therein (third row from top of the PCR results of FIG. 2-*b*). Further, in order to show that the amplified amount is in an equal amount, an amplified amount of β-actin of 356 bp was assessed (lowermost of the PCR results of FIG. 2-*b*). Here, "M" in FIG. 2-*b* stands for a molecular weight marker (HaeIII digest marker), and "*" stands for the results of amplification of plasmid pLPCX-asR70.

```
forward:
                                         (SEQ ID NO: 13)
5'-tgaagtgtgacgtggacatccgc-3' reverse:
                                         (SEQ ID NO: 14)
5'-gccaatctcatcttgttttctgcgc-3'
```

Expression of asR70 was confirmed in the cells other than the cells MJ90 and the cells T8 from the above, and it was clarified that expression was not derived from plasmids, but derived from those incorporated by transformation.

Also, SV40ST was assessed by immunoblotting of the cytoplasm. The results are shown in the lower rows of FIG. 2-*b* (immunoblotting results). As a result, expression of SV40ST of 15 to 20 kD was confirmed in the cells R7S, R7S-1, R7S-2, R7S-3, R7S-1s, R7S-2s, and R7S-3s. Here, in all the cells, as the control, expression of actin was also confirmed (bottom of the immunoblotting results in FIG. 2-*b*).

Example 3

Influences on the Growth of Transformed Cells of Oligonucleotides Derived from Human 28S rRNA The hTERT-immortalized cells T8 used in Example 2 were cultured for 13 months, and thereafter stored in liquid nitrogen. Thereafter, the cells were thawed, replicated several times, and used in the following experiment.

Into the above-mentioned cells T8 was introduced intact pLPCX (pLPCX), asR70-incorporated pLPCX (asR70), asR56-incorporated pLPCX (asR56), asR46-incorporated pLPCX (asR46), or sR70-incorporated pLPCX (sR70), respectively, and the cells obtained were subjected to drug screening with puromycin to select the introduced cells T8, pLPCX, asR70, asR56, asR46, and sR70. The cell growth and the cell density (n=3) were assessed for cell lines after 4.5 months from the introduction. The results are shown in FIG. 2-*c*. Here, the cell growth can be assessed by measuring an increase in cell counts with time of the cells adjusted to a certain number, and the cell density can be assessed by measuring the cell counts occupying a certain area.

From FIG. 2-*c*, in the cells after 4.5 months from the introduction, asR70-introduced cells and asR46-introduced cells had large cell growing rates, and high cell densities. It is suggested from the above that asR70 and asR46 influence the cell growth mechanisms.

Example 4

Colony Formation of Transformed Cells

Into the hTERT-immortalized cells T8 used in Example 2 was introduced intact pLPCX (pLPCX), asR70-incorporated pLPCX (asR70), asR56-incorporated pLPCX (asR56), asR46-incorporated pLPCX (asR46), or sR70-incorporated pLPCX (sR70), respectively, and thereafter the cells other than the cells introduced with intact pLPCX were further subjected to introduction of SV40ST-incorporated pLPCX. Subsequently, the cells were subjected to drug screening with puromycin, to select the introduced cells T8, pLPCX, asR70, asR56, asR46, and sR70. The cells obtained were cultured, and subjected to a colony formation test with the passage of time (n=3). Also, in a case where colony formation was found, the colonies were classified according to their sizes, as "large (l), i.e. a size of 10 times or more of the cells," "middle (m), i.e. a size of 5 to 9 times or so of the cells," and "small (s), i.e. a size of 3 to 4 times or so of the cells." A total number of colonies of large colonies and middle colonies, i.e. l+m, and the number of small colonies, i.e. s, were counted, and an average thereof was obtained. The results are shown in FIG. 2-*d*. In FIG. 2-*d*, "NP" indicates a case where colonies were found but no proliferation or growth was confirmed, and "NC" indicates a case where the number of colonies was not counted.

It can be seen from FIG. 2-*d* that the colony formation in the soft agar was confirmed in the cells asR70 and the cells asR46, so that both of the cells underwent neoplastic transformation. Also, it is suggested that the cells asR46 have a higher neoplastic transformation efficiency than the cells asR70 because the former cells formed a larger number of colonies than the latter. It is suggested from these results that asR70 and asR46 exhibit even higher transformation efficiencies. In addition, it could be confirmed that human diploid fetal lung-derived fibroblast TIG3 cells can be transformed by using asR46, hTERT, and SV40ST (the results not shown). The above cells asR46, hereinafter also referred to as R4S, were isolated, and the clones thereof (R4S-1, R4S-2, and R4S-3) were prepared, and used in the subsequent experiment.

Example 5

Spectral Karyotyping Analysis of Transformed Cells

Five cells each of hTERT-immortalized cells (T8), cells cotransfected with hTERT and asR70 (R7), cells obtained by introducing SV40ST into the cells T8 (T8+ST), and clones of the cells obtained by introducing SV40ST into the cells R7 (R7S-1, R7S-2, and R7S-3) used in Example 2, and the clones of the cells obtained by introducing asR46 and SV40ST into the hTERT-immortalized cells T8 (R4S-1, R4S-2, and R4S-3) used in Example 4 were subjected to spectral karyotyping analysis (SKY, reverse DAPI banding). The results are shown in Table 1, and representative SKY staining images are shown in FIG. 3.

TABLE 1

| Cells | | Karyotype [No. of abnormal karyotypes/ 5 cells analyzed] |
|---|---|---|
| T8 | | 46, XY [5] |
| R7 | | 46, XY [5] |
| T8 + ST | | 46, XY [5] |
| R7S-1 | | 46, XY, −11, + der (11)t(11; 12)(q21; ?) [5] |
| R7S-2 | | 45, XY, del(5)(p?), der (6) t(6; 22)(p?; q?), i (12)(q10), 22 [5] |
| R7S-3 | | 46, XY, −11, + der (11)t(11; 12)(q21; ?) [5] |
| R4S-1 type | A, | 46, XY [3] |
| | B, | 92, XXYY, del(1)(p32) [1] |
| | C, | 92, XXYY, del(2)(p11) [1] |
| R4S-2 type | A, | 46, XY [1] |
| | B, | 46, XY, t(1; 17)(q12; p12) [1] |
| | C, | 46, XY, del(13)(q22), del(17)t(17; 20)(p12; p12) [1] |
| | D, | 46, XY, der(17)t(17; 20)(p12; p12) [1] |
| | E, | 90, XXYY, der(8)t(1; 8)(p12; q25), t(17; 19)(p11; q13) [1] |
| R4S-3 type | A, | 46, XY, der(17)t(7; 17)(q22; p12)t(17; 22)(q25; q13), der(22)t(17; 22)(q25; q13) [2] |
| | B, | 91, XXYY, der(2)del(2)(q10)t(2; 18)(q10; ?), der(17)t(7; 17)(q22; p12)t(17; 22)(q25; q13) × 2, −18, der(22)t(17; 22)(q25; q13) × 2 [1] |

Figure 3:
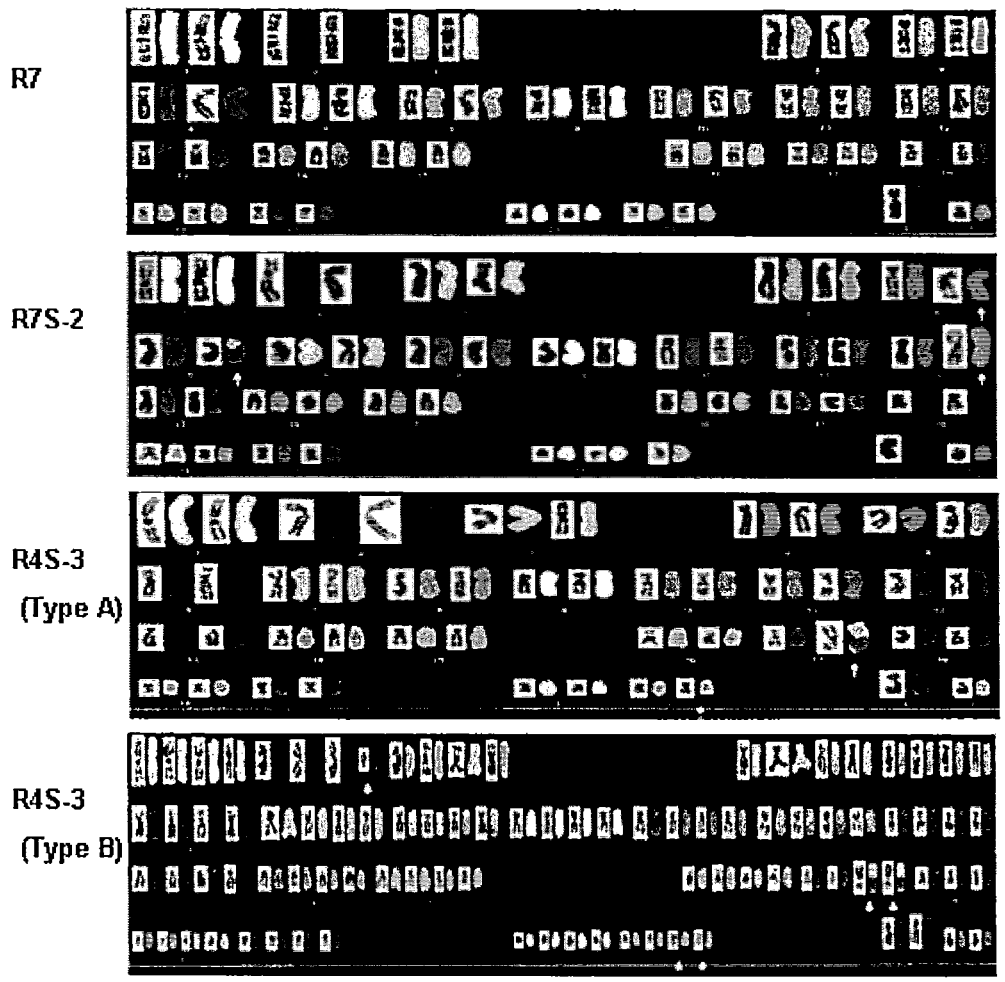
FIG. 3 is views showing the results of spectral karyotype (SKY) image analysis of transformed cells.

From Table 1 and FIG. 3, the cells T8, the cells R7, and the cells T8+ST are confirmed to have 46 chromosome numbers, so that it can be seen that the cells are normal diploid cells. On the other hand, while the cells R7S-1 and the cells R7S-3 are found to have 46 chromosome numbers, apparently, genome rearrangements took place at one site. In addition, the cells R7S-2 were confirmed to have 45 chromosome numbers, one less than the normal cells, and genome rearrangements were confirmed at 4 sites. Also, all of the cells R4S-1, R4S-2, and R4S-3 had diversified chromosome numbers and sites at which genome rearrangements took place, even while the cells were derived from the same cell line, so that several types thereof were confirmed. Among them, the cells R4S-1, R4S-2, and R4S-3 have larger alterations than the cells R7S-1, R7S-2, and R7S-3; however, since normal cells also exist in the cells R4S-1 and R4S-2, it is suggested that these alterations took place after the transformation. It is suggest from the above that cells transfected with hTERT, SV40ST and asR70 are different from the normal cells or cells cotransfected with hTERT and asR70 in the genetic information in the cells.

Example 6

Induction of Endoplasmic Reticulum Stress Response in Transformed Cells

Expression of substances showing endoplasmic reticulum stress response was confirmed on cells T8, pLPCX, asR70, asR56, asR46, and sR70, obtained in the same manner as in Example 4. Also, as to the cells asR70, the same experiments for those cells obtained in the same manner as in Example 2, i.e. cells T8, R7, R7-1, R7-2, R7S, R7S-1, R7S-2, R7S-3, R7S-1s, R7S-2s, and R7S-3s.

Concretely, in accordance with the pulse-chase labeling and immunoprecipitation method with $^{35}$S-methionine, expression levels in extracellular matrix fibronectin (FN), integrin beta 1 (integrin β1) transmembrane receptor, and endoplasmic reticulum resident chaperone Bip for each of the cells. The results on the cells T8, pLPCX, asR70, asR56, asR46, and sR70 are shown in FIG. 4-a.

Figure 4A:
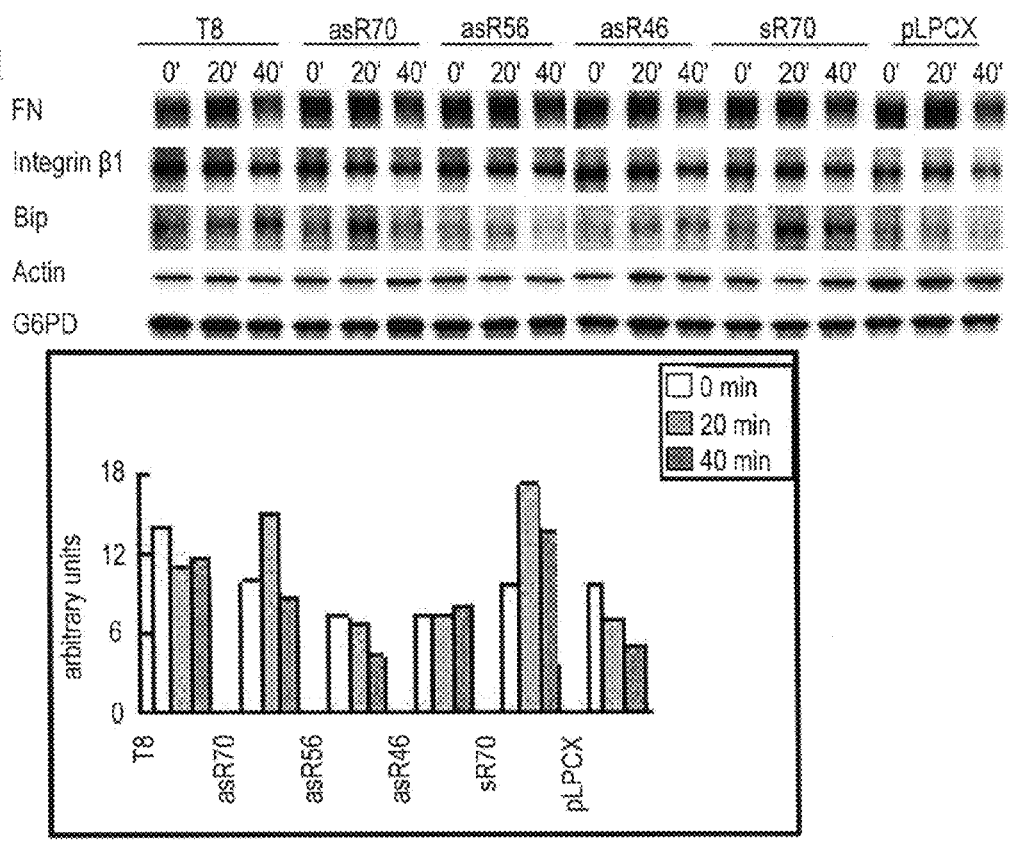
FIG. 4 is views showing the results of inhibition of the Bip protein synthesis and the induction of endoplasmic reticulum stress response.
Figure 4B:
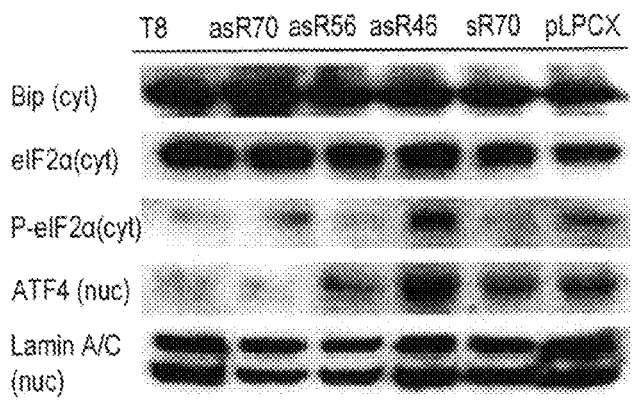
Figure 4C:
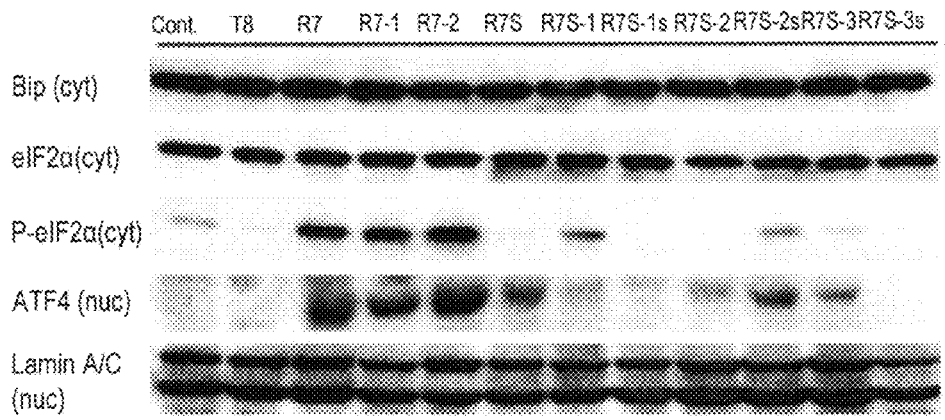

It could be seen from FIG. 4-a that expression levels of Bip are lowered with passage of time in the cells asR70, the cells asR56, the cells asR46, and the cells pLPCX (see the graph circumscribed with box in FIG. 4-a). On the other hand, expression levels of the FN and the integrin β1 were shown to have the same tendencies as signal-independent actin or glucose 6-phosphate dehydrogenase, so that hardly any changes were found therewith. While expression levels of FN and integrin β1 were not found to show any changes because of high productivity in the cells, expression levels of Bip were found to show some changes; therefore, it is suggested that Bip synthesis is inhibited in ribosomes of the cells asR70, the cells asR56, and the cells asR46.

In addition, in order to further study the influences of Bip in more detail, the same studies were conducted on the cytoplasmic proteins. Concretely, 30 μg of a cytoplasmic protein was separated by 10% SDS/PAGE, and Bip, eIF2a (eukaryotic initiation factor 2a), phosphorylated-eIF2a (P-eIF2a), and ATF4 (activating transcription factor 4) were immunoblotted. The results on the cells T8, pLPCX, asR70, asR56, asR46, and sR70 are shown in FIG. 4-b, and the results on the cells T8, R7, R7-1, R7-2, R7S, R7S-1, R7S-2, R7S-3, R7S-1s, R7S-2s, R7S-3s are shown in FIG. 4-c. Here, if the Bip synthesis is inhibited, a so-called endoplasmic reticulum stress response is induced, in which eIF2a is phosphorylated to inhibit protein synthesis, and the phosphorylated eIF2a initiates the translation of ATF4.

According to FIGS. 4-b and -c, the expression levels of Bip and eIF2a were nearly of the same level in all the cells, but expression of phosphorylated eIF2a was more markedly confirmed in the cells asR46, the cells R7, the cells R7-1, and the cells R7-2, and induction of ATF4 accompanying therewith was also confirmed. It is suggested from the above that asR46 and asR70 inhibit Bip synthesis, thereby inducing the endoplasmic reticulum stress response.

Example 7

Screening of Anticancer Agent

Cells introduced with hTERT, SV40ST, and a human 28S rRNA-derived oligonucleotide are cultured in a cell culture equipment, and a solution prepared by dissolving a candidate compound in a solvent is added thereto, and the cells are further cultured. On the other hand, using a group with no addition of a candidate compound as a control, in cases where changes such as transformed morphological losses, induction of apoptosis, and losses of anchorage-independent growth of the cells are found to be greater than the group with no addition, the candidate compound added to the cells can be judged to have a high possibility of possessing an action as an anticancer agent.

The method for preparing neoplastically transformed cells from human-derived cells of the present invention can be utilized when a variety of human normal cells are induced to be neoplastically transformed in order to elucidate cancer onset mechanisms, so that the method can be effectively utilized in search of target molecules for a new medicament.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

SEQUENCE LISTING FREE TEXT

SEQ ID NO: 1 of the Sequence Listing is an antisense oligonucleotide asR70 derived from human 28S rRNA;

SEQ ID NO: 2 of the Sequence Listing is an antisense oligonucleotide asR46 derived from human 28S rRNA;

SEQ ID NO: 3 of the Sequence Listing is a partial nucleotide sequence of transforming RNA;

SEQ ID NO: 4 of the Sequence Listing is a partial nucleotide sequence of human 28S rRNA;

SEQ ID NO: 5 of the Sequence Listing is a partial nucleotide sequence of human SRP RNA;

SEQ ID NO: 6 of the Sequence Listing is an antisense oligonucleotide asR56 derived from human 28S rRNA;

SEQ ID NO: 7 of the Sequence Listing is an oligonucleotide sR70 derived from human 28S rRNA;

SEQ ID NO: 8 of the Sequence Listing is a partial nucleotide sequence of human 28S rRNA;

SEQ ID NO: 9 of the Sequence Listing is a modified sequence of the partial nucleotide sequence of transforming RNA;

SEQ ID NO: 10 of the Sequence Listing is a primer for pLPCX-retroF;

SEQ ID NO: 11 of the Sequence Listing is a primer for asR70 cDNA;

SEQ ID NO: 12 of the Sequence Listing is a primer for pLPCX-seqR;

SEQ ID NO: 13 of the Sequence Listing is a primer for β-actin; and

SEQ ID NO: 14 of the Sequence Listing is a primer for β-actin.

What is claimed is:

1. A method for inducing neoplastic transformation of isolated human fibroblast cells in vitro, the method comprising introducing into said human fibroblast cells a recombinant vector expressing a human telomerase catalytic subunit (hTERT) gene product and an SV40 small T antigen (SV40ST) gene product, and an antisense oligonucleotide complementary to a sense sequence of a human 28S ribosomal RNA (rRNA), wherein said antisense oligonucleotide is selected from the group consisting of the nucleotide sequence of SEQ ID NO: 1, SEQ ID NO: 2 and SEQ ID NO: 6, wherein said antisense oligonucleotide binds to the sense sequence of the rRNA, wherein transformed cells have anchorage-independent growing ability and show chromosomal aberrations, thereby undergoing neoplastic transformation.

2. The method according to claim 1, wherein the antisense oligonucleotide consists of the nucleotide sequence of SEQ ID NO: 1.

3. The method according to claim 1, wherein the antisense oligonucleotide consists of the nucleotide sequence of SEQ ID NO: 2.

4. The method according to claim 1, wherein the antisense oligonucleotide consists of the nucleotide sequence of SEQ ID NO: 6.

5. The method according to claim 1, wherein the introducing is by an electroporation method, a calcium phosphate method, or a lipofection method.

* * * * *

```
                        SEQUENCE LISTING

<160> NUMBER OF SEQ ID NOS: 14

<210> SEQ ID NO 1
<211> LENGTH: 70
<212> TYPE: RNA
<213> ORGANISM: Homo sapiens

<400> SEQUENCE: 1
ccggggaggg gggaggacgg ggagcggggg agagagagag agagagggcg cggggugggg     60
agggagcgag                                                           70

<210> SEQ ID NO 2
<211> LENGTH: 46
<212> TYPE: RNA
<213> ORGANISM: Homo sapiens

<400> SEQUENCE: 2
gggaggacgg ggagcggggg agagagagag agagagggcg cggggu                   46

<210> SEQ ID NO 3
<211> LENGTH: 9
<212> TYPE: RNA
<213> ORGANISM: Artificial Sequence
<220> FEATURE:
<223> OTHER INFORMATION: A partial nucleotide sequence of Transforming
      RNA

<400> SEQUENCE: 3 ggagaggaa                                                             9

<210> SEQ ID NO 4
<211> LENGTH: 4
<212> TYPE: RNA
<213> ORGANISM: Homo sapiens

<400> SEQUENCE: 4 cucc                                                                  4

<210> SEQ ID NO 5
<211> LENGTH: 4
<212> TYPE: RNA
<213> ORGANISM: Homo sapiens

<400> SEQUENCE: 5
```

```
gagg                                                                  4

<210> SEQ ID NO 6
<211> LENGTH: 56
<212> TYPE: RNA
<213> ORGANISM: Homo sapiens

<400> SEQUENCE: 6
ccggggaggg gggaggacgg ggagcggggg agagagagag agagagggcg cggggu        56

<210> SEQ ID NO 7
<211> LENGTH: 70
<212> TYPE: RNA
<213> ORGANISM: Homo sapiens

<400> SEQUENCE: 7
cucgcucccu ccccaccccg cgcccucucu cucucucucu ccccgcucc ccguccuccc    60 cccucccccgg                                                         70

<210> SEQ ID NO 8
<211> LENGTH: 6
<212> TYPE: RNA
<213> ORGANISM: Homo sapiens

<400> SEQUENCE: 8 cucucu                                                              6

<210> SEQ ID NO 9
<211> LENGTH: 9
<212> TYPE: RNA
<213> ORGANISM: Artificial Sequence
<220> FEATURE:
<223> OTHER INFORMATION: A modified nucleotide sequence of Transforming
      RNA

<400> SEQUENCE: 9 gagagagag                                                           9

<210> SEQ ID NO 10
<211> LENGTH: 19
<212> TYPE: DNA
<213> ORGANISM: Artificial Sequence
<220> FEATURE:
<223> OTHER INFORMATION: primer for pLPCX-retroF

<400> SEQUENCE: 10
cgctagcgct accggactc                                                19

<210> SEQ ID NO 11
<211> LENGTH: 27
<212> TYPE: DNA
<213> ORGANISM: Artificial Sequence
<220> FEATURE:
<223> OTHER INFORMATION: primer for asR70 cDNA

<400> SEQUENCE: 11
ataaagcttc tcgctccctc cccaccc                                       27

<210> SEQ ID NO 12
<211> LENGTH: 17
<212> TYPE: DNA
<213> ORGANISM: Artificial Sequence
<220> FEATURE:
<223> OTHER INFORMATION: primer for pLPCX-seqR
```

```
<400> SEQUENCE: 12
tggggtcttt cattccc                                                      17

<210> SEQ ID NO 13
<211> LENGTH: 23
<212> TYPE: DNA
<213> ORGANISM: Artificial Sequence
<220> FEATURE:
<223> OTHER INFORMATION: primer for beta-actin

<400> SEQUENCE: 13
tgaagtgtga cgtggacatc cgc                                               23

<210> SEQ ID NO 14
<211> LENGTH: 25
<212> TYPE: DNA
<213> ORGANISM: Artificial Sequence
<220> FEATURE:
<223> OTHER INFORMATION: primer for beta-actin

<400> SEQUENCE: 14
gccaatctca tcttgttttc tgcgc                                             25
```